United States Patent [19]

Handley et al.

[11] Patent Number: 5,177,059
[45] Date of Patent: Jan. 5, 1993

[54] POLYMYXIN B CONJUGATES

[75] Inventors: Dean A. Handley, Mountain Lakes; Philip Lake, Parsippany, both of N.J.

[73] Assignee: Sandoz Ltd., Basel, Switzerland

[21] Appl. No.: 608,080

[22] Filed: Nov. 1, 1990

Related U.S. Application Data

[63] Continuation-in-part of Ser. No. 437,487, Nov. 15, 1989, abandoned.

[51] Int. Cl.$^5$ .................. A61K 37/10; A61K 37/02; C07K 5/00; C07K 7/00
[52] U.S. Cl. ............................. 514/8; 514/11; 530/317; 530/319; 530/322
[58] Field of Search ............... 514/8, 11, 12; 530/322, 530/317, 319

[56] References Cited

U.S. PATENT DOCUMENTS 4,766,106  8/1988  Katre et al. .................. 514/12

FOREIGN PATENT DOCUMENTS 22711    2/1977  Australia .
0147761  4/1985  European Pat. Off. .
2342740  8/1977  France .
89016389B 3/1989  Japan .

OTHER PUBLICATIONS

Snezhko et al., 1972, Moscow Textile Institute, 1972, pp. 1–8.
Zalipsky et al, Eur. Polym J., vol. 19, No. 12, 1983, pp. 1177–1183.
LaPort et al, Biochemistry, vol. 16, No. 8, 1977, pp. 1642–1648.
Biosis Abstract 85:421296 Kitagawa et al. 1985 "Sensitive Enzyme Immunoassay of Colistin . . . " *J. Assoc. Off. Anal. Chem.* 68(4):661–664.

*Primary Examiner*—Lester L. Lee
*Assistant Examiner*—A. M. Davenport
*Attorney, Agent, or Firm*—Gerald D. Sharkin; Robert S. Honor; Carl W. Battle

[57] ABSTRACT

Polymyxin B carrier conjugates, especially polymyxin B-dextran, are water soluble, have a greater half-life in the bloodstream and are significantly less toxic than native polymyxin B.

16 Claims, No Drawings

POLYMYXIN B CONJUGATES

This application is a continuation-in-part of U.S. application Ser. No. 07/437,487 and now abandoned, filed Nov. 15, 1989.

This application relates to novel polyxmyxin B conjugates and to methods of using these novel conjugates.

Endotoxins or lipopolysaccharides are structural molecules derived from the cell walls of the Gram-negative bacteria. When introduced into the bloodstream, they can interfere with the regulation of body temperature and cause fever. They also have a toxic effect, leading to cardiac, pulmonary and kidney failure. Endotoxin-related diseases are a leading cause of death among those patients in intensive care units.

Unique among antibiotics is the ability of polymyxin B (PMB) to neutralize endotoxin, accomplished by binding to the lipid A region of the endotoxin molecule. Polymyxin B from *B. polymyxa* (*B. aerosporus*) is a highly charged amphiphilic cyclic peptidolipid. It is also useful in combating various fungal infections, especially those arising in immunocompromised individuals. However, PMB has some properties which renders it less than an ideal antibiotic. First, it has a short half-life in the body, requiring repeated dosages in order to be effective. Secondly, as it passes through the kidney it can cause extensive damage. Thirdly, at high doses it possesses neurotoxic properties which cause respiratory paralysis.

Previously, researchers have conjugated PMB to immobile or fixed molecules. See for example, Issekutz, 1983, *J. Immumol. Methods* 61: 275-281, describing the binding of PMB to Sepharose. These conjugates, while useful in purification techniques, are not suitable for in vivo therapeutic use.

One approach to achieve pharmacological activity, increased duration, or decreased organ toxicity has involved the conjugation of drugs to large molecular weight macromolecules such as dextran, polyethylene glycol, or polyvinylpyrrolidine. Attempts in this area of polymer conjugation have been met with only limited success, however. For example, the conjugated form of procainamide (an antiarrythmic drug) was less active and exhibited a shorter half life than native procainamide (Schacht et al. 1985. *Ann N.Y. Acad. Sci.* 446:199-211). Similarly, a prostaglandin analog B245, linked to a carrier, was less effective (by several log orders) than the native molecule (Bamford et al. 1986. *Bioch. Biophys. Acta* 886: 109-118). Reductions in biological potency have also been described for conjugated forms of kallikrein, aprotinin, bradykinin (Odya et al. 1978. *Biochem. Pharmacol.* 27: 173-179), the anti-tumor drugs daunorubicin (Hurwitz et al. 1980. *J. Appl. Biochem.* 2: 25-35), and mitomycin c (Takakura et al. 1984 *Cancer Res.* 44: 2505-2510). Conjugated enzmes also suffer a reduction in biological activity due to steric hindrance and reduced substrate accessibility (Blomhoff et al. 1983. *Biochem. Biophys. Acta* 757: 202-208; Marshall et al. 1976. *J. Biol. Chem.* 251(4): 1081-1087; R. L. Foster, 1975. *Experientia* 31(7): 772-3; Wileman et al. 1983 *J. Pharm. Pharmacol.* 35: 762-765). There are, however some examples of improvements in circulatory half-life after conjugation (Wileman, supra; Kaneo 1989. *Chem. Pharm. Bull.* 37(1) 218-220.)

It would be desireable to develop a form of PMB which would stay in the blood stream longer, and/or does not have neuro- or nephrotoxicity at therapeutic doses.

DESCRIPTION OF THE INVENTION

This invention relates to water-soluble PMB-carrier conjugates which are useful in neutralizing endotoxin. They are an improvement over the administration of native PMB because they are substantially less toxic than PMB yet retain PMB-activity.

As used throughout the specification and claims, the following definitions will apply:

$LD_0$ is the highest non-toxic dose of PMB or its conjugate.

$LD_{100}$ is the dose of PMB or its conjugated form which results in 90-100% lethality when injected into a normal test animal.

$PD_{100}$ is the dose of polymyxin B or its conjugated form which, when injected into a hypersensitized test animal, results in at least 95% survival.

Therapeutic Index (TI) is calculated by dividing $LD_{100}$ by $PD_{100}$.

The carrier which can be conjugated to PMB may be chosen from molecules which can form water-soluble conjugates and which are uniform, non-toxic, non-carcinogenic, non-irritating, and non-immunogenic. Such carriers include polysaccharides such as dextran, hydroxy ethyl starch (HES), proteins such as albumin, and polymers such as polyvinyl-pyrrolidone, polyethylene glycol, and polyvinyl alcohol. Dextran is the most preferred.

The size of the biopolymer portion of the conjugate may vary. Typically it will range from a molecular weight of 25,000 to 500,000, preferably from 50,000 to 300,000. The size of the biopolymer chosen can significantly contribute to the duration of the conjugate's effective time of circulation in the blood stream. Generally the larger the biopolymer, the longer the conjugate will stay in circulation. Thus the size of the biopolymer can be adjusted to result in a conjugate whose time of duration in the body corresponds to a predetermined time.

Polymyxin B has five γ-amino groups which bind to the bacterial endotoxin. At least one γ-amino group can be used to securely bind the PMB to the carrier, but all five sites cannot be used for this purpose, or the conjugate will lack endotoxin-neutralizing activity. Various chemical reactions can be used to conjugate polymyxin to these carriers. The number of PMB molecules bound per molecule of polymer can be influenced by varying the ratios of reactants during the coupling reaction. Generally the conjugate will contain between 1 PMB:15 biopolymer to 200 PMB:1 biopolymer, more preferably the conjugate will have from 1-10 PMB:1 biopolymer, and even more preferably from 1-3 PMB:1 biopolymer. The conjugates with high PMB:biopolymer ratios seem to possess greater potency than conjugates with lower ratios.

One method of making the PMB-carrier conjugate, more specifically, the PMB-dextran conjugate, is through carbamate linkages. PMB-dextran conjugates made in this fashion (detailed in Example 1, below) are found to retain the anti-endotoxin activity of native PMB, and in addition are found to be devoid of the acute neurotoxicity exhibited by native PMB. These conjugated forms also showed a 2-5 fold improved therapeutic index by decreasing chronic toxicity over that of native PMB.

A second method of making conjugated PMB-dextran is through an amine bond. PMB-dextran conjugates made in this manner (detailed in Example 2, below) retained the same general anti-endotoxin activity or were more active than native PMB. These conjugated forms were completely devoid of any acute neurotoxicity seen by native PMB and exhibited a 33-fold improvement of the therapeutic index by reducing chronic toxicity over that seen with native PMB. In particular, one PMB-dextran conjugate was devoid of any measurable toxicity at the doses tested and retained good anti-endotoxin activity, resulting in an 80-fold improvement in the therapeutic index.

Further, it has been suprisingly found that conjugates produced by this method and "rapidly processed" exhibited a 60–120-fold improvement in TI. "Rapidly processed" as used throughout the specification and claims means that the material was separated from unbound PMB using molecular sieving chromatography, de-salting gels, or Amicon ultrafiltration, for approximately 12–24 hours, preferably approximately 18 hours (as opposed to an extended dialysis time of 7–10 days). Thus conjugates produced by these methods and rapidly processed comprise another aspect of this invention.

The PMB conjugate obtained from either of the two methods outlined above has proven difficult to purify. Initially, a 10-day extended dialysis was tried in order to separate native PMB from the conjugate. Although the protein level inside the dialysis bag reached an asymptote, and gel permeation column chromatography showed a single large molecular weight species, the material still contained unbound PMB. Even when Amicon pressure filtration was substituted for extended dialysis the results were the same. Conjugates purified in this mannter were equipotent to PMB, but still retained ⅛ to 1/5 the toxicity of PMB. While not intending to be bound by theory, it appears that there is some chemical association between the "free" PMB and the conjugate which renders its separation difficult. Upon injection in the animal, the "free" PMB dissociates itself and causes toxicity problems.

Applicants have developed the following procedure which obviates the above difficulties. PMB-dextran conjugates are precipitated in a lower alcohol, preferably methanol or ethanol, especially ethanol, followed by centrifugal collection and ultrasonic resolubilization. This process is repeated at least 3 times and preferably 7–10 times and the resulting material is evaluated for purity by gel permeation chromatography and reverse phase high pressure liquid chromatography (RP-HPLC). If protein is detected by either method, the precipitation-resolubilization procedure is repeated. Conjugate purified in this manner is referred to throughout the specification as "ultra pure" PMB-conjugate and generally can be described as having less than 20 $\mu$g unconjugated PMB per 1 mg total protein, and preferably less than 10 $\mu$g unconjugated PMB per 1 mg total protein.

Ultra-pure PMB-conjugate has virtually no toxicity and as a result, applicants have been unable to establish a $LD_{100}$ for it. At a dose of 100 mg/kg, no toxicity was seen. At higher concentrations the solution was too viscous to inject. This is in contrast to native PMB which has a $LD_0$ i.v. of 5 mg/kg and a $LD_{100}$ i.v. of 9.5 mg/kg. Thus the Therapeutic Index of ultra-pure PMB-conjugate is over 1000-fold higher than native polymyxin B, due to decreased toxicity.

A second advantage in using the conjugate rather than native PMB is that the conjugate has a longer duration of activity and thus can be used prophylactically. Thus one aspect of this invention is the prevention of diseases caused by the presence of bacterial endotoxin by administering to a human or animal in need of such prophylactic treatment a prophylactically-effective amount of a soluble conjugate of PMB and a carrier, particularly dextran and an inert solution. As the PMB-conjugate has virtually no toxicity it can be prophylactically administered on a routine basis to patients who might be susceptible to septic shock, such as those dependent upon liquid food for long-term nourishment.

Yet another aspect of this invention is the treatment of diseases caused by the presence of bacterial endotoxin comprising administering to an animal or human in need of such treatment an endotoxin-neutralizing amount of the soluble conjugate of PMB and a carrier, particularly dextran, and an inert solution. As PMB is also effective in combating bacterial or fungal infections, another aspect of this invention is a method of treating bacterial or fungal infections comprising administering to an animal or human in need of such treatment a fungicidally-effective amount of a water-soluble conjugate of PMB and a carrier, particularly dextran, and an inert solution.

The PMB-carrier conjugate of this invention can be used in a manner consistent with the use of PMB itself, i.e. it can be used alone as an antibiotic for bacterial or fungal infections or combined with other bacteriocidal agents and/or anti-inflammatory agents. It may be administered in any of the forms by which native PMB is conventionally administered, i.e. intramuscularly, intravenously, intrathecally, subconjunctivally or topically. Thus formulations for intramuscular injections typically comprise an effective amount of PMB-conjugate in sterile water, physiological saline or approximately 1% procane.HCl. Intravenous formulations typically comprise an effective amount of PMB-conjugate in 5% dextrose and sterile water. Intrathecal formulations typically comprise an effective amount of PMB-conjugate in physiologic saline. For topical ophthalmic use, an effective amount can be mixed with water or physiologic saline, and optionally glycerine, and cupric sulfate for eye drops, or it may be made into an ointment or suspension. Creams, for topical applications, especially for burned areas, typically comprise an effective amount of PMB-conjugate in a base of inactive ingredients such as liquid petrolatum, propylene glycol, polyoxyethylene polyoxypropylene, and emulsifying wax.

The amount of PMB-conjugate to be used is based on the amount of native PMB which would typically be prescribed for a particular patient (taking into account such factors as the condition being treated, and age and weight of the patient), and the activity of the particular PMB-conjugate used. Often, a dosage reduction of up to 50% compared to native PMB can be realized due to the effective increased activity of the PMB conjugate, its reduced toxicity and its increased duration of activity.

The invention is better illustrated by reference to the following non-limiting Examples.

EXAMPLE 1

Chemical Conjugation of PMB to Dextran (Method A)

2 g dextran (79,000 or 200,000 MW) is dissolved in 20 ml water, cooled to 0° C., and 5-300 mg of 1-cyano-4-dimethylamino pyridinium tetrafluoroborate (CDAP) is added and mixed for 30 seconds. Triethylamine (0.2M, 0.04 ml per 5 mg CDAP) is added dropwise with vigorous stirring, and the entire reaction mixture is transferred to 80 ml of ice cold absolute ethanol containing 1 ml of 10N HCl. The dextran precipitates, and the precipitate is removed by centrifugation at $1000 \times g$, for 5 min at 0° C., and resolubilized in 20-50 ml of 0.25M Na-bicarbonate buffer at pH 9.0. To this mixture 600-1000 mg of PMB (either powdered or presolubilized in water) is added and stirred for 24 hours at 8° C. The entire reaction mixture is then transferred to a 50,000 molecular weight cut-off dialysis tubing and dialyzed against 0.05M pyrogen-free phosphate buffer for 6-10 days. The final dialyzed reaction mixture is measured for protein content by spectrophotometry at 208 nm absorbance or at 595 nm using the Bradford reagent (Bio Rad, Richmond, Calif.).

Free amino groups are determined using the ninhydrin reaction, with native PMB as a control. Analysis for nitrogen and carbon content is done using a CHN Elemental Analyzer.

In the table below, "molar ratio" is determined by dividing the amount of dextran used in conjugation (23.7 $\mu$mol) by the final PMB-protein in $\mu$mol (based on 208 nm analysis) after dialysis. Dextran is abbreviated "dx". The "C:N" ratio assumes 450 molecules of water per 2 g dextran. The "bonds/PMB" is an estimate of the number of bonds by which PMB is attached to dextran, based on the ninhydrin reaction. "ND" is "not determined".

| SUMMARY OF CONJUGATION REACTIONS | | | |
|---|---|---|---|
| RXN | CDAP | MOLAR RATIO | C:N RATIO | BONDS/PMB |
| A | 21 $\mu$mol | 1 dx:0.23 PMB | ND | ND |
| B | 106 $\mu$mol | 1 dx:1.62 PMB | 1 dx:1.52 PMB | 3.0 |
| BB | 106 $\mu$mol | 1 dx:1.95 PMB | 1 dx:1.90 PMB | 1.1 |
| C | 532 $\mu$mol | 1 dx:3.70 PMB | 1 dx:3.25 PMB | 3.0 |
| CC | 532 $\mu$mol | 1 dx:4.99 PMB | 1 dx:5.00 PMB | 2.2 |
| D | 1064 $\mu$mol | 1 dx:6.62 PMB | 1 dx:8.70 PMB | 1.65 |
| DD | 1064 $\mu$mol | 1 dx:8.81 PMB | ND | 1.3 |
| E | 2128 $\mu$mol | 1 dx:10.9 PMB | ND | 2.1 |

EXAMPLE 2

Chemical conjugation of PMB to dextran (Method B)

1.25 g dextran (79,000 or 200,000 MW) is dissolved in 20 ml of distilled water after which 0.071-0.71 g Na-periodate is added. After 1 hr at 22° C., the reaction mixture is transferred to a column containing DEAE A25 cationic exchange resin (Pharmacia Inc., Piscataway, N.J.) and the mixture is collected and pooled to a single fraction of 20-25 ml. The oxidized dextran is then mixed with 2 g PMB dissolved in 80-200 ml Na-bicarbonate or Na-borate buffer (pH 8.5-9.0) and after 60 minutes, 40 ml 0.05-25% Na borohydride either in a single treatment or in multiple treatments, each treatment lasting 30 min. to 24 hrs. is added. This reaction proceeds for 30 min, and then was dialyzed for 7-10 days at 8° C. against 0.05M pyrogen free Na-phosphate buffer. The final dialyzed reaction mixture was analyzed for protein content, free amino groups as described in Example 1.

In addition to purification by extended dialysis, several representative reactions were rapidly purified using dialysis for 18 hours, purified on a G-100 Sephadex column (Pharmacia, Inc., Piscataway, N.J.) and concentrated on an Amicon filtration unit using a YM-100 Amicon filter.

In the table below, the molar ratio is determined by dividing the amount of dextran used in conjugation (6.25 $\mu$mol) by the $\mu$mol final PMB protein (based on the 208 nm data) after dialysis. The percent nitrogen is determined using a CHN elemental analyzer. Bonds/PMB is estimated by the ninhydrin reaction.

| SUMMARY OF CONJUGATION REACTIONS | | | | |
|---|---|---|---|---|
| RXN | NaIO$_4$ (g) | MOLAR RATIO | % nitrogen | BONDS/PMB |
| 1/50 | 0.014 | 1 dx:3.64 PMB | 0.21 | 3.6 |
| 1/10 | 0.071 | 1 dx:12.9 PMB | 1.05 | 2.9 |
| 1/5 | 0.142 | 1 dx:26.8 PMB | 1.71 | 2.6 |
| 1/4 | 0.178 | 1 dx:29.8 PMB | 2.76 | 3.0 |
| 1/2[1] | 0.355 | 1 dx:39.6 PMB | 3.74 | 2.2 |
| stock* | 0.710 | 1 dx:151 PMB | 6.91 | 4.0 |

*Reaction mixture was turbid and remained so after dialysis
[1]Purified using rapid dialysis

EXAMPLE 3

Anti-endotoxin activity of PMB-conjugates

A. Endotoxin-induced lethality

Male CB57BL/c mice (18-22 g, Jackson Labs) are used throughout this study. Animals are given endotoxin (0111B$_4$ from List Biologicals, Palo Alto, Calif.) and galactosamine to hypersensitize, as described in Galanos et al., 1979. *Proc. Natl. Acad. Sci. USA* 76: 5939. The endotoxin and galactosamine (320 mg/kg) are injected intraperitoneally in 0.5 ml pyrogen-free isotonic saline per animal between 13:00 and 15:00 to avoid diurnal variation. From a dose-response study, it is determined that 0.01 mg/kg endotoxin produces 85-95% lethality. Animals are observed each day for 6 days after injection.

B. PMB (native and conjugated forms) induced lethality

PMB (native and conjugated forms) are evaluated for their inherent toxicity in non-sensitized mice. Male CB57BL/c mice (18-22 g, Jackson Labs) are used throughout this study. Animals are given either native PMB or conjugated PMB by intraperitoneal injection (0.5 ml/animal) and lethality monitored for 7 days. The LD$_{100}$ is determined by varying the dose of PMB (native and conjugated forms) that result in 100% lethality. From 10-20 animals are used for each dose.

C. PMB anti-endotoxin evaluations

PMB (native and conjugated forms) are evaluated for their ability to neutralize endotoxin by either pre-mixing with endotoxin for 60 minutes before i.p. injection or by coadministration of the substances as a single i.p. injection. While the concentration of the PMB (native and conjugated forms) are varied, the volume of each injection is kept constant at 0.5 ml per animal. The protection by the conjugated PMB was compared to the native PMB (in terms of mg protein/kg). Controls (endotoxin, galactosamine, and vehicle) are included as well in each study. Each group has between 10-17 animals.

The Protective Dose (PD$_{100}$) is defined as that dose of PMB (either native or conjugated) that results in greater than 95% survival. Statistical analyses of survival between groups or in relation to controls is performed using a Chi-square analysis using the Yate's correction for continuity.

D. Determination of Therapeutic Index

The Therapeutic Index (TI) for PMB (native and conjugated) forms is determined by dividing the $LD_{100}$ by the $PD_{100}$. In the table below, the "treatment" refers to the conjugates appearing in Examples 1 and 2, supra.

| TREATMENT | ANTI-ENDOTOXIN DATA | | |
|---|---|---|---|
| | $LD_{100}$MG/KG | $PD_{100}$MG/KG | TI |
| Native PMB[1] | 25 | 2 | 12.5 |
| Native PMB[2] | 25 | 2 | 12.5 |
| A | >30 | 1 | >30 |
| B | >28 | >2 | >14 |
| C | ND | 5 | ND |
| D | 140 | 2 | 70 |
| 1/5 | 83 | 0.2 | 415 |
| 1/2[1] | ~40-60 | 0.05 | 800-1200 |
| stock[2] | >212 | 0.2 | >1060 |
| stock[3] | >212 | 20 | >10.6 |

[1]Rapidly-purified material
[2]The PMB or conjugate is allowed to react with the endotoxin for 60 min before i.p injection
[3]The PMB or conjugate is injected simultaneously with the endotoxin

EXAMPLE 4

1. Obtaining "ultra pure" Polymyxin-B conjugates

Polymyxin B-conjugates are prepared essentially as described in Example 2, supra, to obtain conjugate designated RXN 1/50.

The conjugate, a white flocculant, is precipitated in 60% ethanol, collected by centrifugation, and then subjected to ultrasonic resolubilization. This process is repeated seven times and the resulting material is evaluated for purity by gel permeation chromatography and reverse phase high pressure liquid chromatography (RP-HPLC). Although no free PMB is detected by gel permeation chromatography, RP-HPLC shows 48 μg unconjugated PMB per 1 mg of total protein. The conjugate is then subjected to 3 additional precipitations to remove the unconjugated PMB.

The resulting "ultra pure" PMB-conjugate is compared to native PMB in an endotoxin-induced leathality test as described in Example 3C supra.

At 1 mg/kg i.v., the ultra-pure PMB-conjugate gave >70% protection against a $LD_{90}$ endotoxin challenge for at least 6 hours. At 10 mg/kg i.v., this conjugate provided therapeutic protection 1.5 hours after administration of the endotoxin. Therefore the PMB-conjugate is suitable for prophylactic use.

The "ultra pure" PMB-conjugate has a suprising reduction in toxicity as compared with native PMB. Native PMB has an $LD_0$ i.v. of 5 mg/kg and an $LD_{100}$ i.v. of 9.5 mg/kg, suggesting an early onset of toxicity and narrow therapeutic range. The ultra-pure PMB-conjugate has an $LD_0$ i.v. of >100 mg/kg, and we have been unable to establish an $LD_{100}$, due to its inherent non-toxicity. Comparisons in the table below are made between the highest non-toxic dose of PMB (native or conjugated).

| TREATMENT | $LD_0$MG/KG[1] | $PD_{100}$MG/KG[2] | TI |
|---|---|---|---|
| PMB | 5 | 0.1 | 50 |
| Ultra-pure conjugate | >100 | 0.1 | >1000 |

[1]PMB (native or conjugate) given by i.v. injection and lethality monitored over 7 days. $LD_0$ is the highest non-toxic dose which can be injected into a normal test animal
[2]PMB (native or conjugate) given by i.v. injection 1-3 minutes before an $LD_{100}$ i.p injection of E.coli 0111B4 endotoxin (0.5 μg/kg)

What is claimed is:

1. A conjugate comprising Polymyxin B and a carrier, wherein said conjugate is soluble in water and of a size suitable for delivery and circulation in the blood stream of a human or animal, said conjugate having anti-endotoxin activity and comprising a molecular ratio of said Polymyxin B to said carrier from about 1:15 to about 200:1.

2. A conjugate according to claim 1, wherein the carrier is selected from the group consisting of dextran, polysaccharides, hydroxyethyl starch, protein, albumin, polyvinylpyrrolidone, polyethylene glycol, and polyvinyl alcohol.

3. A conjugate according to claim 2 wherein the carrier is dextran.

4. A conjugate according to claim 3 wherein the ratio of PMB to dextran molecules is from 1-3 PMB:1 dextran.

5. A conjugate according to claim 3 wherein the dextran has a molecular weight of from approximately 25,000 to 500,000.

6. A conjugate according to claim 5 wherein the dextran has a molecular weight of from 50,000 to 300,000.

7. A conjugate according to claim 6 wherein the dextran has a molecular weight of from 79,000 to 200,000.

8. A conjugate according to claim 3 wherein the PMB is attached through carbamate linkages.

9. The conjugate according to claim 3 wherein the PMB is attached to the dextran through amine bonds.

10. Polymyin B-dextran conjugate produced by a process comprising:
   a) conjugating PMB to dextran to form a PMB-dextran conjugate; said conjugate comprising a molecular ratio of PMB to dextran from about 1:15 to about 200:1 and being soluble in water and of a size suitable for delivery and circulation in the blood stream and
   b) purifying said conjugate by precipitating the conjugate in a lower alcohol;
   c) resuspending the conjugate; and
   d) repeating steps b) and c) until the conjugate is substantially free from unbound PMB.

11. A conjugate according to claim 10 wherein steps b) and c) are repeated at least 3 times.

12. A method of treating diseases caused by the presence of bacterial endotoxin comprising administering to a human or an animal in need of such treatment an endotoxin-neutralizing amount of a conjugate of claim 1.

13. A method of treating a fungal injection comprising administering to a human or an animal in need of such treatment a fungicidally effective amount of a conjugate of claim 1.

14. A method of treating a bacterial infection comprising administering to a human or an animal in need of such treatment a bacteriocidally effective amount of a conjugate of claim 1.

15. A method of preventing disease caused by the presence of bacterial endotoxin comprising administering to a human or animal a prophylactically-effective amount of a conjugate of claim 1.

16. An injectable form of the polymyxin B-dextran conjugate of claim 1 which is substantially non-toxic.

* * * * *